United States Patent [19]
Aspden et al.

[11] Patent Number: 5,824,087
[45] Date of Patent: Oct. 20, 1998

[54] BONE REGENERATION

[75] Inventors: Richard Malcom Aspden, Ellon; Srimathi Rajagopalan Murali; Richard William Porter, both of Aberdeen, all of Scotland

[73] Assignee: Aberdeen University and Plasma Biotal Limited, United Kingdom

[21] Appl. No.: 727,396
[22] PCT Filed: Apr. 10, 1995
[86] PCT No.: PCT/GB95/00815
    § 371 Date: Jan. 21, 1997
    § 102(e) Date: Jan. 21, 1997
[87] PCT Pub. No.: WO95/27518
    PCT Pub. Date: Oct. 19, 1995

[30] Foreign Application Priority Data
Apr. 11, 1994 [GB] United Kingdom ............. 9407135

[51] Int. Cl.⁶ ........................................ A61F 2/28
[52] U.S. Cl. .................. 623/16; 606/94; 606/100; 604/264
[58] Field of Search ................ 606/92, 93, 94, 606/99, 100; 623/16; 604/264, 274

[56] References Cited

U.S. PATENT DOCUMENTS

| | | | |
|---|---|---|---|
| 4,274,163 | 6/1981 | Malcom et al. | 606/94 |
| 4,619,655 | 10/1986 | Hanker et al. | 623/1 |
| 5,147,403 | 9/1992 | Gitelis | 623/16 |
| 5,306,303 | 4/1994 | Lynch . | |
| 5,431,639 | 7/1995 | Shaw | 604/264 |
| 5,702,446 | 12/1997 | Schenck et al. | 623/16 |

FOREIGN PATENT DOCUMENTS

| | | | |
|---|---|---|---|
| 0006430 | 1/1980 | European Pat. Off. | 623/16 |
| 0 369 603 A1 | 10/1989 | European Pat. Off. . | |
| 0 520 237 A2 | 6/1992 | European Pat. Off. . | |
| 0 530 804 A1 | 9/1992 | European Pat. Off. . | |
| 0 616 814 A1 | 3/1994 | European Pat. Off. . | |
| 2 690 332 | 10/1993 | France . | |
| 35 05 567 A1 | 6/1986 | Germany . | |
| 4313201 | 11/1994 | Germany | 623/16 |

OTHER PUBLICATIONS

Damien et al., "Investigation of a hydroxyapatite and calcium sulfate composite supplemente with an osteoinductive factro", *Journal of Biomedical Materials Research*, 1990, 24(6): 369–354.

Najjar et al., "Enhanced osseointegration of hydroxylapatite implant material", *Oral Surg Oral Med Oral Pathol*, 1991; 71(1); 9–15.

*Primary Examiner*—Paul B. Prebilic
*Attorney, Agent, or Firm*—Law Office of Jane Massey Licata

[57] ABSTRACT

An intraosseous device having an elongated shaft and handle with a syringe attached to the shaft is disclosed. The syringe can be filled with an intraosseous liquid suspension which is made of a hydroxyapatite, a carbonated apatite, a calcium ion source, and a hormone mixture. The shaft includes a frusto-conical connector for releasable interconnection with cortical bone, and the handle facilitates turning the shaft to interconnect it to the bone.

9 Claims, 6 Drawing Sheets

BONE REGENERATION

This application is a national stage 35 USC 371 application of PCT/GB95/00815 filed Apr. 10, 1995.

The present invention relates to a method, apparatus and composition for bone regeneration including the treatment of osteoporosis. Osteoporosis affects an increasing number of an aging population, particularly the female elderly. It is mediated at least in part by genetic defects and a fall in circulating oestrogen levels. Although calcium replacement therapy can have some beneficial effects, the larger doses of calcium involved have other less helpful consequences and accordingly, the prognosis for those with bone demineralisation is not particularly good.

Bone formation in old age is a significant problem since not only does bone regrow more slowly in the elderly, but complications are likely to set in. For this reason, a fracture of for example a femur, tibia, etc, in the elderly is serious and can lead to morbidity.

Currently, no direct means exist to increase bone density of for example, the femur neck, trochanter, etc. There exists, therefore, a need for a facile means of increasing bone density particularly in important skeletal areas without significant surgery.

The invention has its genesis in the discovery that an intraosseous composition may be injected into a desired site, which composition then acts to increase density without rejection problems; being swiftly incorporated into the osseous matrix.

Animal studies, particularly in the rat and rabbit, have shown that hydroxyapatite (HA) is a potent osteoconductive material. When surgically reconstructing the skull, zygoma and mandible, HA has been used as a bone graft substitute acting as scaffolding to support new bone growth. It has also been used to fill cavities after excision of bone cysts, as a graft to restore depressed tibial fractures, in cervical interbody fusion, and as a coating on prostheses. Implanted into canine long bones, HA increases the compressive strength of the cancellous bone and increases the bending strength of cortical bone.

We have now however found that HA may be injected in a liquid form and that there is an advantage of a combining HA, and calcium sulphate (CS) with distilled water. Such a liquid composition sets rapidly, somewhat like Plaster of Paris, and the CS is gradually resorbed in-vivo leaving the porous HA with a large surface area for osteoconduction. CS alone is a known osteoconductive medium being slowly absorbed by an advancing front of new bone and indeed, Najjar, et al. in Oral surgery, Oral medicine, Oral pathology, 1991; 1971(1): 9–15have demonstrated that the additional of CS to HA improved its working properties without adversely affecting its osteointegration and said composite showed a higher rate of bone ingrowth than HA alone.

This indeed has been shown in U.S. Pat. No. 4,619,655 (Hanker) which reveals the use of calcium sulfate with hydroxyl apatite as a repair composition for damaged bone. Further in U.S. Pat. No. 5,147,403, free-flowing calcium sulfate has been described for the conjunction of a prosthesis to host bone.

It has also been shown in the rabbit, that certain proteins, in that case bovine osteogenic factor, are osteoinductive which when added to osteoconductive material, lead to an enhancement of bone ingrowth. (Damien, et al., Journal of Biomedical Materials Research, 1990, 24(6): 369–54.)

Bone is an essential requirement for several different surgical procedures such as spinal fusion, hip arthroplasties, the treatment of some types of fractures and in the management of tumour surgery.

Presently bone is usually obtained from the patient as an autogenous graft. The iliac crest is a common site for harvesting of such bone but there are several problems with this procedure. In the first place, the length of the surgical procedure is significantly increased if bone has to be harvested and indeed damage to the sacroiliac joint can occur thereby. There is a risk of damage to neural and vascular structures in that area and there is a significant risk of long term pain along the scar line of the patient. Further, hernia through the bone defect may occur and there are limits to the quantity of the bone which can thereby be obtained. Accordingly, bone graft substitute are being increasingly used to reconstitute bone defects. Hydroxy apatite along with calcium sulfate as shown above acts as a mineral scaffolding into which new bone can grow. Further when hydroxy apatite is used to coat implants such as a femoral component of a hip replacement, there is clear evidence to show that bone ingrowth occurs into the hydroxy apatite layer over time.

EP-A-0520237 discloses that HA and other calcium phosphate materials are potent osteoconductive materials in solid shaped or flowable form. Similarly, EP-A-0530804 provides a matrix forming material such as HA along with an angiogenic factor and the osteogenic factor. U.S. Pat. No. 5306303 provides a method of inducing bone growth by implanation of a bone morphogenetic protein-free ceramic.

We have shown that hormones selected from a human bone morphogenic protein, human growth hormone (HGH), IGF-1 and 2 are useful additions to such compositions as well as TGF-beta. HGH is a potent anabolic hormone for calcium and bone metabolism. It stimulates osteoblastic proliferation and differentiation in-vitro and increases the protection of IGF-1 and 2, both of which have profound effects on osteoblasts.

In a first aspect of the invention, there is provided an intraosseous injection device including an introducer means comprising;

an elongate shaft provided with a through bore terminating at a distal end in a frusto-conical connector portion for interconnection with cortical bone, and handle means associated with said shaft to enable the shaft to be screwed into the cortical bone in use. The handle may extend perpendicularly to the axis of the shaft, preferably adjacent to the proximal end thereof. The connector may be screw-threaded and may be such that when the nozzle of the shaft comes into contact with the cortical bone, under a single turn will lock the shaft into the bone into the cortical bore.

The proximal end of the shaft may terminate in a hub, said hub defining a recessed portion for the releasable engagement of manipulatable parts. Said manipulatable parts may include a needle carrying hub provided with a hollow vented double needle, through which passes the injectable composition with an annular space to allow venting of blood and fat from the bore. Alternatively or additionally, the manipulatable portions may include a guide wire carrying hub, for purposes elucidated below. Further the needle carrying hub may be provided with a proximal chamber for operative interengagement with a syringe. The syringe may be adapted to inject the intraosseous composition and may include means whereby the needle may be withdrawn during the injection sequence, so that intraosseous liquid is applied under pressure over a selected length of a bore in an osseous matrix.

Devices of the foregoing type may be used with an intraosseous injectable composition which comprises carbonated apatite (CA) and/or hydroxyapatite (HA) and a biocompatible source of calcium ions, for example, calcium sulphate (CS) or tricalcium phosphate, monocalcium phosphate, monohydrate or calcium carbonate which may further include a hormone selected from HGH, IGF-1 and 2 wherein "IGF" means insulin-like growth factors. The above identified composition may be in the form of a settable injectable liquid. It is known that calcium sulphate (CS) is rapidly setting, but the present invention allows compositions in accordance with the invention to be injected under pressure, to set when injected and subsequently to be resorbed quickly and effectively.

It is preferred that the additive hormone is human growth hormone (HGH) and preferably the HGH is a recombinant HGH.

The CA or HA may have a particle size of between 30–300 μm although a range of 70 to 250 μm is to be preferred, thereby to obtain a spacing in situ of about 200–250 μm between adjacent HA particles. This allows for excellent bone regrowth characteristics.

In a particularly preferred form of the invention, the composition comprises 10% to 90% HA, 90% to 10% calcium salt, and up to 4 units (preferably 2 or 3 units) of the HGH morphogenic protein; the balance being of distilled water or saline.

In a preferred embodiment, the ratio may be 1 part of CA or HA to 3 to 3.5 parts of CS. In the preferred settable composition, 40 to 70%, and preferably 50–60% of the weight of the composition is distilled water; the balance being of the solid components.

The calcium salt, especially if CS, may be of a modified fast or slow setting type. If fast setting, the composition may be made with relatively more water. The fast setting compositions so made have the advantage that they set quickly after injection thereby controlling the way the settable composition behaves in the bore after injection, for example, preventing or indeed encouraging dispersion as required.

According to a further aspect of the present invention, there is provided a process for positioning of a intraosseous solution in bone which comprises;

(a) inserting a drill tipped guide wire under a remote control into a bone site with rotation, (b) utilising a cannulated drill to provide a bore to said site along said guide wire, (c) removing said drill along said guide wire, (d) introducing a vented double injection needle into said bore and injecting a composition as set forth above thereinto and subsequently withdrawing said needle and allowing said composition to set.

The step of introducing the injection needle may include driving means for operatively connecting the injection means to the bore to allow the composition to be introduced under pressure. The injection means may be a syringe which comprises, or is operatively associated with, a frusto-conical screw-threaded nozzle which is adapted to engage with the neck of a bore in cortical bone by simple rotation under mild pressure.

Many types of fractures are presently being treated by holding the two fractured pieces together by means of a metal screw and/or plate. Some examples of such fractures are a fixation of a non-union of (a) scaphoid fractures, (b) fixation of fractures of medial and lateral malleoli of the ankle and (c) fixation of fractures of the olecranon.

There are several problems with the use of metal screws essentially because it is a foreign material and is susceptible to infection which may require further surgery and removal. Further, such metal items may loosen in the long run and may be counter productive to the healing of the fracture.

In another aspect of the invention, there is provided a shaped osseous prosthesis adapted to enter fully into a bore in an osseous matrix which-prosthesis comprises hydroxyapatite (HA) and a biocompatable source of calcium ions, said prosthesis cooperatable in said bore so as to provide immediate support to said matrix. In a preferred form of the invention, this prosthesis is either provided with a hormone selected from HGH, IGF-1 and 2, described above or is used with an injectable admixture as described above which is relatively rich in one of said hormones, such that the combination of the prosthesis and the injected material together comprise a described number of units of hormone. For HGH, this may be 2–4 units. This arrangement may replace or supplement a metal screw and is with time integrated into the bone. This alleviates some of the common complications such as loosening and other failures, thus reducing morbidity associated with. metal screws.

The shape of the implant should be such as to provide a sliding fit within a bore in an osseous matrix. The outside diameter, may for example be a clearance fit for a bore of 4 to 5 mm, or indeed up to 10 mm. The shaped prosthesis may have a helical, longitudinally or annularly ribbed configuration. It preferably has common transverse cross-section, but may taper, for example, toward the distal end.

The composition forming the prosthesis may consist of HA and/or CA and CS, but preferably includes HGH or other promoters of hormone growth as herein discussed. It may also include other pharmaceutically acceptable excipients in addition to distilled water or saline. The prosthesis is preferably inserted into a bore in an osseous matrix along with, or after, the administration of an intraosseous injectable composition so that together the two forms of composition form a coherent structurally significant intraosseous support assembly. The intraosseous injected material as herein before set forth and the prosthesis may then be introduced into the bore via the introducing device.

The invention will now be described, by way of illustration only, with reference to the accompanying drawings, and with reference with the following examples.

In the accompanying drawings,

FIG. 17 shows diagrammatically a hole drilled in a femur to inject materials.

Figure 1:
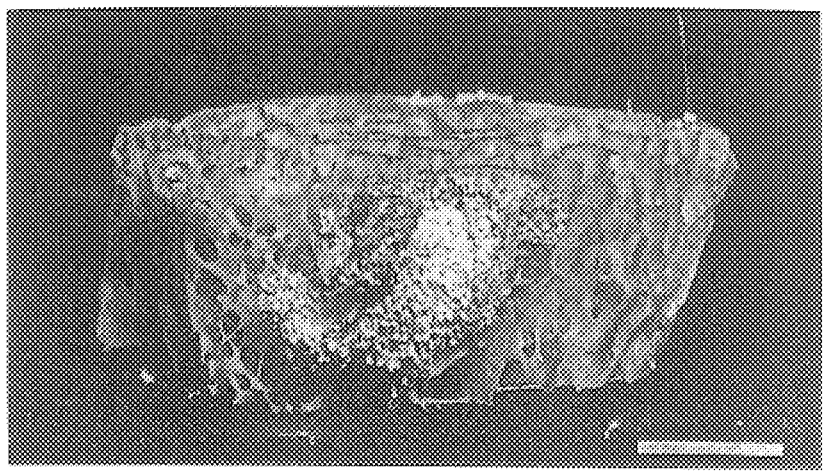
FIG. 1 shows the macroscopic appearance of a freeze-fractured bone section showing the injected material, within osteoporotic trabecula bone (Bar=5 mm).
Figure 2:
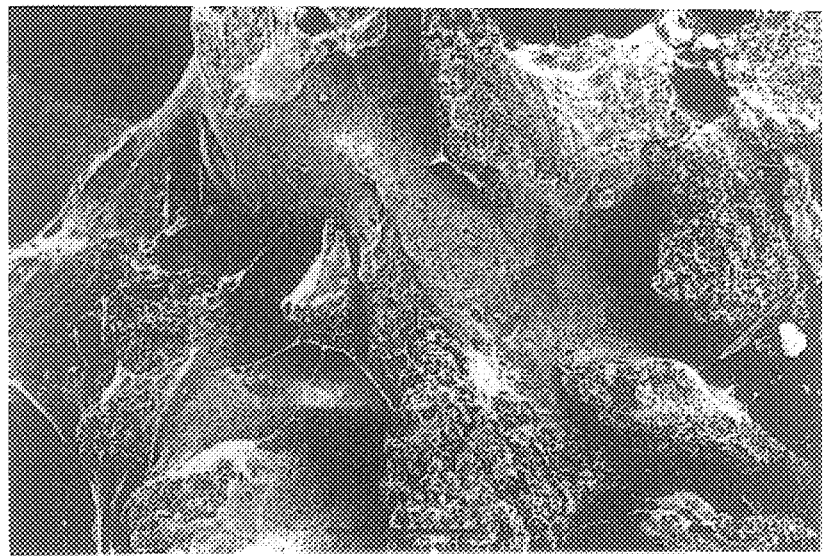
FIG. 2 shows dense bone surrounding the HA particles. In this region the CS has disappeared. (Bar line equals 200 μm)
Figure 3:
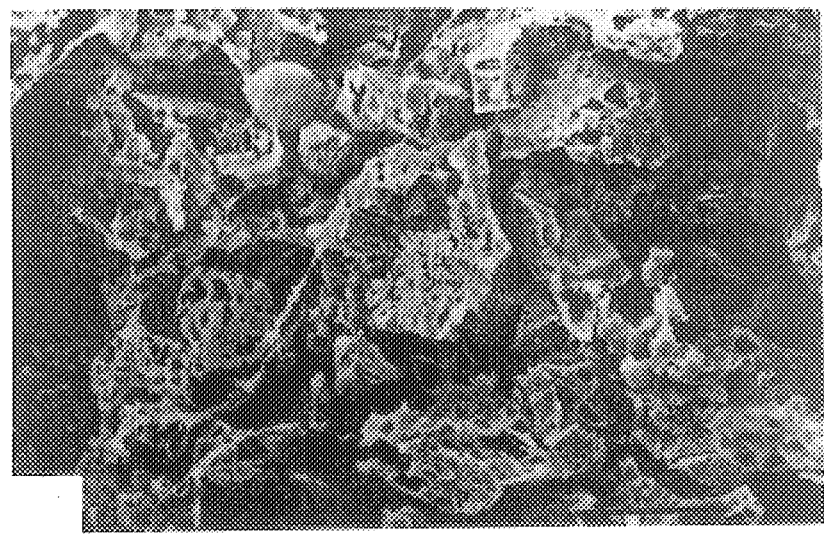
FIG. 3 shows crystals of CS, the surface of which show an eroded appearance with holes. A fine network of new bone can be seen across the CS crystals. (Bar line equals 20 μm)
Figure 4:
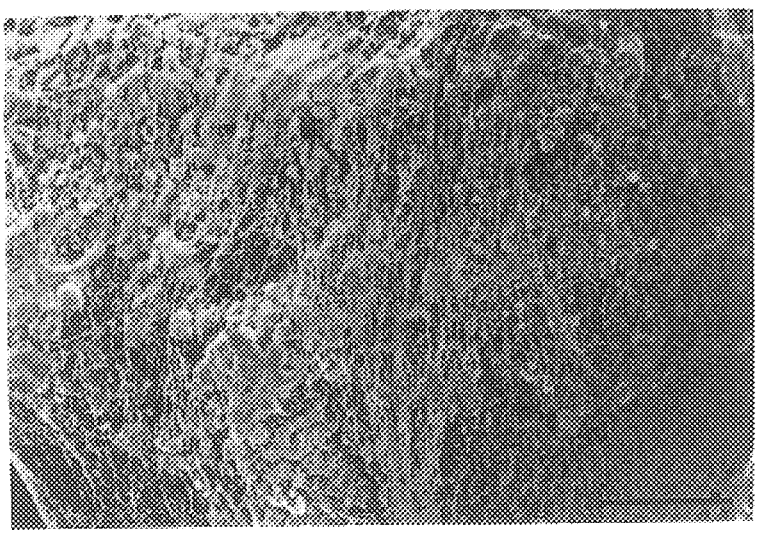
FIG. 4 shows a fine network of woven bone surrounding HA particles. (Bar line equals 10 μm)
Figure 5:
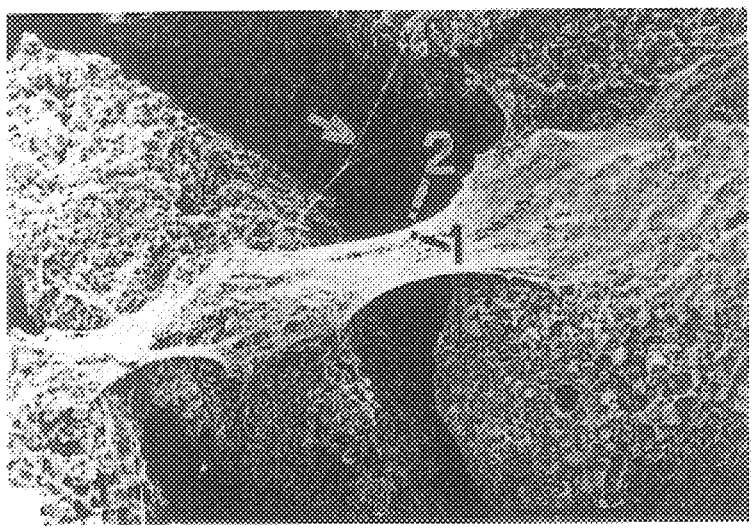
FIG. 5 shows a bridge of woven bone across HA particles. (Bar line equals 50 μm)
Figure 6:
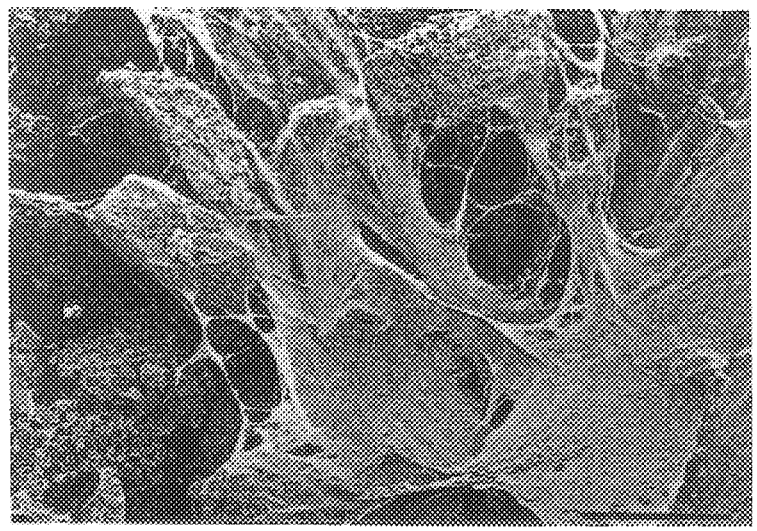
FIG. 6 shows sheets of calcified material across HA particles. (Bar line equals 300 μm)
Figure 7:
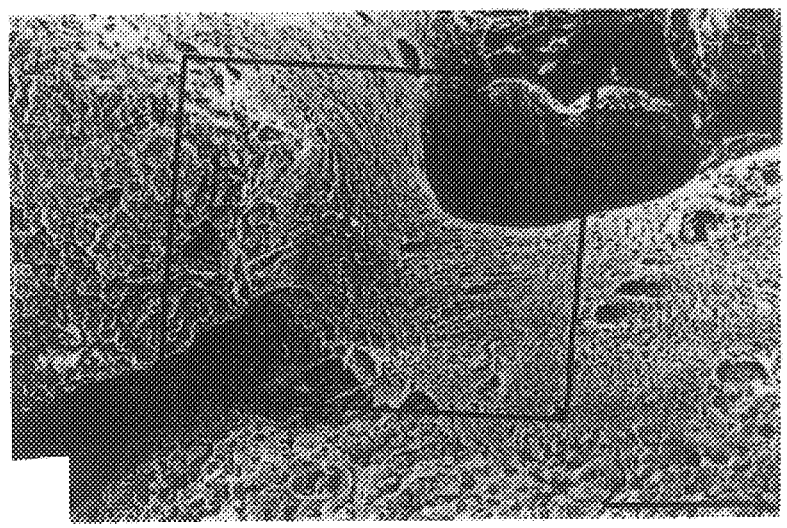
FIG. 7 shows new bone bridging from an original trabeculum on the right hand of the figure to a particle of HA. (Bar line equals 100 μm)
Figure 8:
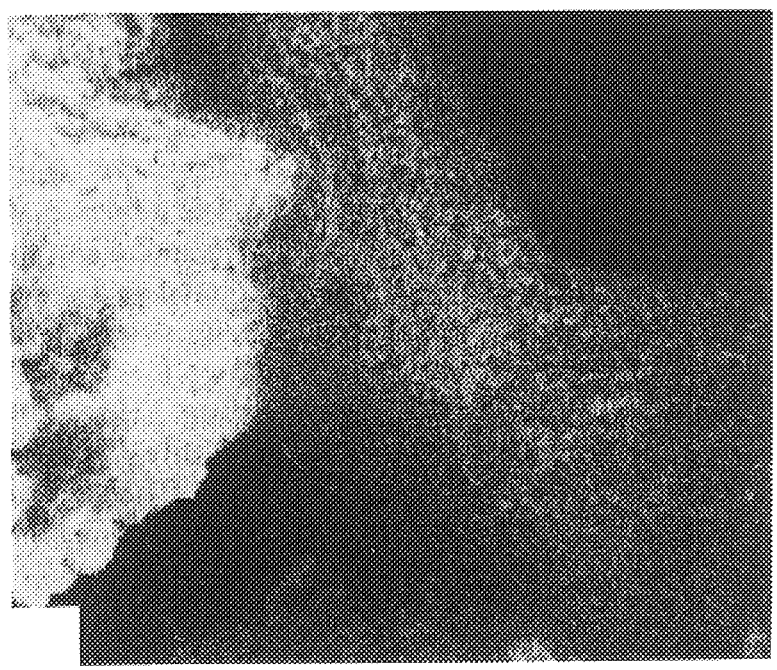
FIG. 8 shows part of FIG. 7 at a higher magnification showing new bone linking across an HA particle to old trabecula bone. (Bone line equals 50 μm)
Figure 9:
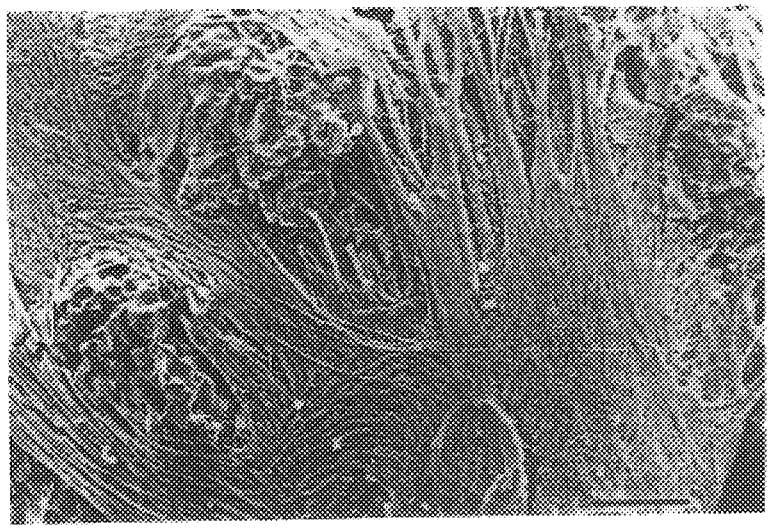
FIG. 9 shows bonding of new bone onto HA particles. (Bar line equals 50 μm)
Figure 10:
FIG. 10 shows bunches of small crystals in the network of the bone. (Bar line equals 3 μm)
Figure 11:
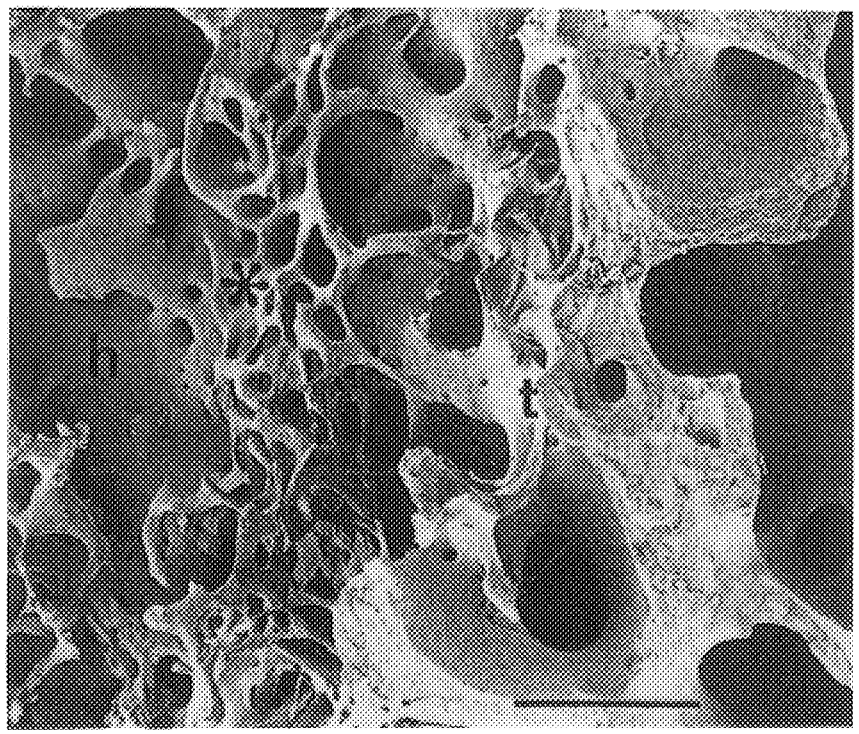
FIG. 11 shows new bone formation (*) at the margin between the drill hole (h) where no injected material is present and old trabecula bone (t). Trabeculae broken by the drill have been covered by a thin layer of new bone. (Bar line equals 1 mm)
Figure 12:
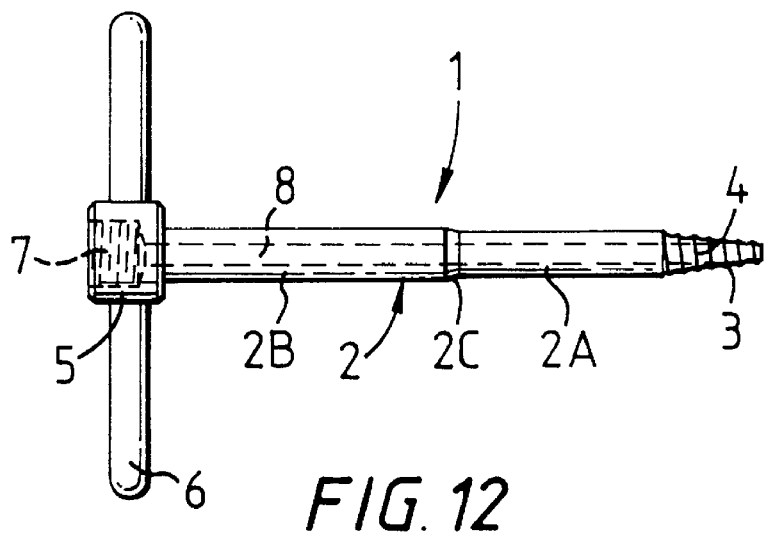
FIGS. 12–16 show side views in part transverse cross section of an introducer assembly in accordance with the present invention and FIG. 17 shows diagrammatically the use of the introducer assembly of FIG. 12–16 within a femur head.

With reference to FIGS. 12–16, the main introducer 1 is shown in FIG. 12 and comprises a shaft shown generally at 2, with shaft portions 2A as a distal shaft portion, shaft portion 2B as a proximal shaft portion, and shaft portion 2C as a ridge portion disposed between the distal and proximal portions to 2A and 2B. The shaft 2A terminates at the distal end in a nozzle portion 3 provided with a frusto-conical screw-thread portion 4. Although bore 8 extends from the nozzle portion 3 along the axis of the introducer 1.

Figure 13:
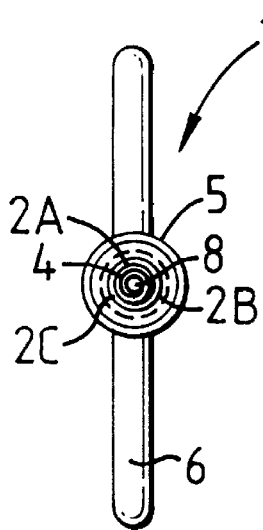

The proximal end of the introducer 1 is provided with a hub from which extend handles 6; said handles 6 extending perpendicular to the axis of the shaft 2 and the hub 5. The shaft 2 is formed integrally with, or attached to, the hub 5 so that the bore 8 extends throughout the length thereof. The bore 8 terminates at the proximal end in an axial chamber 7 having an internal configuration to be described subsequently. An end-on view of the arrangement of FIG. 12 is shown in FIG. 13.

Figure 14:
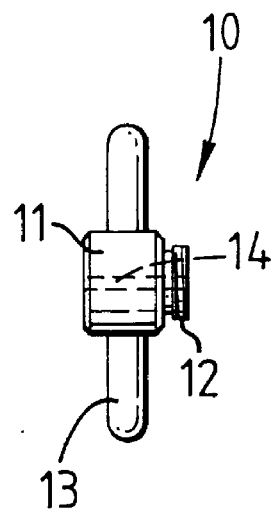
Figure 15:
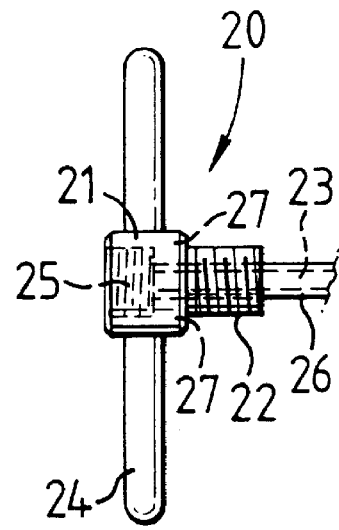

The main introducer 1 may be utilised either with a guide wire carrier of FIG. 14 or with a needle carrier of FIG. 15.

Figure 16:
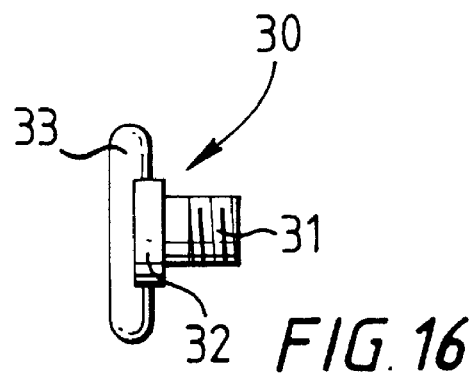

With reference to FIG. 14, a guide wire carrier 10 is provided with a hub 11 similar to that shown in FIG. 16 and similarly provided with handles 13 extending perpendicular to the axis of the hub 11. The hub 11 is also provided with a central annulus 12 for location within the axial chamber 7 of the introducer 1. The guide wire carrier 10 is provided with an axial through bore 14 to accommodate a drill tipped guide wire.

With reference to FIG. 15, a needle carrier 20 is again provided with a hub 21. Hub 21 provides handles 24 extending perpendicular to the axis of said hub 21. The distal end of the hub 24 is provided with a centering annulus 22 through which passes a through bore 23 for a vented double needle 26. The through bore 23 terminates within the hub 21 in an axial chamber 25 for cooperation with a syringe. The hub 24 is provided with a plurality of radially extending vents 27 which connect with the outer sheath of the double needle 26.

Finally, with reference to FIG. 16, a stopper 30 is provided with a hub 32 from which extends in an axial direction a plug member for interengagement with an axial chamber of the needle carrier 20. On the proximal side of the hub 32, are handle members 33. It will be observed that the plug member of the stopper 30 may operatively interengage in the axial chamber 25 of the needle carrier 20. Further, it will be noted that either of the centering annulus 22 of the needle carrier, or the centering annulus 12 of the guide wire carrier can locate within the axial chamber 7 of the introducer 1.

Figure 17:
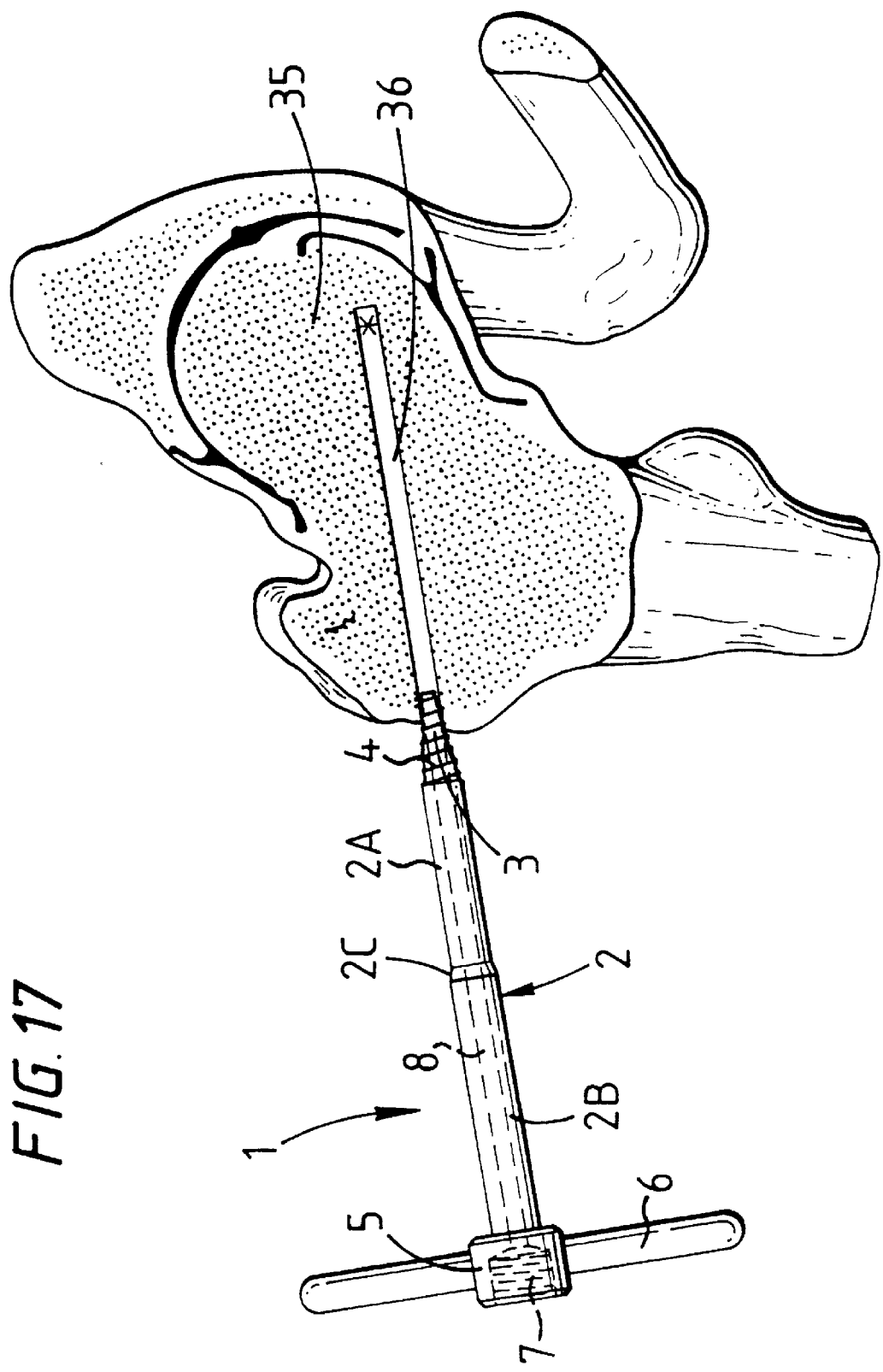

The modus operandi of the device is best shown in FIG. 17. Additionally to the features already described, there is shown therein a femur head 35 and a bore 36.

Using a local anaesthetic, an incision is made down to the femur as shown. A drill tipped guide wire is inserted under rotation and fluoroscopic control along the femoral neck into the femoral head to a desired site. A cannulated drill is passed over the guide wire and a bore, large enough to freely accept the injection needle, is drilled into the femoral head.

With the drilling complete, the drill is withdrawn and the main introducer 1 is passed over a guide wire such that the through bore 8 extends about the guide wire and through the guidewire carrier 10 whereby the nozzle portion 3 is led into contact with the outer edge of the cortical bone of the femur 35. The handle 6 may then be rotated under a little pressure so that after about one turn, the device will lock the nozzle 3 into the neck of the bore 36. In this connection, it will be noted that the bore in this instance is 4.5 mm whereas the end of the nozzle is 4.25 mm.

An injection needle having an internal diameter of about 4 mm and a length of about 30 cm is passed through the bore 8 and over the guide wire and into the bore in the femur head (36) and the guidewire is then withdrawn. Material as set forth above can then be injected from the syringe which fits onto the end of the double needle 26 and locates in the axial chamber 7. As can be seen by FIG. 15, the double needle is connected to the axial chamber 25 so that the composition according to the present invention may be delivered under pressure and such pressure may be maintained, even when the double needle is partially withdrawn by inserting plug member 31 of the stopper 30 into the axial chamber 25 of the needle carrier 20. It will be appreciated that blood and fat etc., can vent to the exterior via the double needle and the vents 27.

Example 1

A study was conducted in order to consider the effects of injecting bioactive materials into the osteoporotic proximal femur. Of the patients treated, one elderly lady died from unrelated causes sixteen weeks after injection.

Prior to the injection, a composition comprising 1 part HA to 3.25 CS, and 2 units HGH were admixed with about 60% distilled water to produce fine liquid paste. This substance was rapidly charged into a syringe and used within 10 minutes. The patient, treated as described in FIG. 17, was first established with the introducer device 1 secured to a blind bore 36 through the neck of the femur 35. The syringe was then introduced into the axial chamber 25 of the needle carrier 20 disposed on the introducer 1 and the material injected under pressure. The needle (26) is a ready fit in the bore 36, and hence any excess pressure within the bone is relieved via the double needle 26 and vents 27. The composition according to the present invention may thus be injected into the bone matrix as shown. By sealing the back pressure at the axial chamber 7, it is possible by means of the syringe to raise the pressure at the distal end of the bore 36 thereby causing the mixture to flow into the osteoporotic bone. Further, the needle and syringe can be gradually withdrawn leaving a column of composition in accordance to the present invention within the bone. With the needle withdrawn, the introducer is counter-rotated to remove it from contact with the bone and the incision suitably sutured.

An elderly lady treated as above died sixteen weeks after treatment from unrelated causes. This gave an opportunity to monitor the results of the injection in the human body by scanning electron microscopy. It was shown, as exemplified in the attached FIGS. 1 to 11, that there was abundant new bone formation across the 4.5 mm drilled hole. New bone engulfed the particles of HA and linked with the peripheral trabeculae. The CS had largely been resorbed. There appeared to be a graduation of change from the periphery of the hole where there were fixed bridges of new bone to the centre where there was a fine network of new bone between the particles. The proximal, unfilled portion of the drill hole acted as a convenient control and demonstrated that without the injected material, apart from a thin peripheral rim of new bone, the hole remained vacant.

The results from this patient show that a mixture of HA, CS and GH is a potent stimulus for bone formation in the elderly osteoporotic female. HA seems to provide an important scaffolding on which new bone will quickly bond. Although the CS had been largely resorbed within the sixteen weeks, it provides a useful high concentration of calcium. At the same time, the following observations were made.

(a) Hydroxyapatite. The particles of HA did not show an changes in their appearance from the pre-injection studies. Many particles were however largely engulfed by new bone, particularly at of the periphery site (C4).

(b) Calcium sulphate. Most of the particles had disappeared after sixteen weeks and those that remained had an eroded surface (see FIG. 5). Some areas showed an aggregation of new flake-like crystals, one of which had a spiral configuration (see FIG. 6). X-ray micro analysis confirmed that these crystals contained calcium, sulphur and oxygen.

(c) New bone formation. There was abundant new bone formation found in between the injected material, extending across the diameter of the 4.5 mm drilled hole. Towards the centre of the hole containing the injected material, there were many areas of a fine net-like structure (see FIG. 9) surrounding the HA particles. In other areas, this net appeared to have coalesced to form solid bridges or sheets between the HA particles (see FIGS. 7 and 8). At the edge of the drilled hole, the bone formation was dense and had engulfed many of the particles of HA. It linked with and was not distinguishable from, normal trabeculae. There was a clear bonding in the new bone and the HA (see FIGS. 10 and 11).

(d) X-Ray Micro Analysis. This was used to determine the nature of the materials. Spectra from the material engulfing and bridging HA particles contained calcium, oxygen and phosphorus; indistinguishable from those obtained from old trabecula bone. The absence of carbon confirmed that the new bridging structures were not residual undigested organic material. At higher magnifications, it was possible to identify bunches of small crystals at some positions within the network of new bones. X-ray microanalysis showed that these contained calcium, phosphorus and oxygen with no evidence of sulphur or carbon. This probably demonstrates the early stages of bone formation (see FIG. 9).

(e) The proximal centimetre of the drill hole in the head was not filled with injectable material. Although there was a thin rim of new bone round the periphery of the hole, the remaining space was unfilled and not bridged with any new bone.

Example 2

In a further example, a helically shaped prosthesis was formed of HS and CS with sufficient distilled water to form a mouldable paste. The helically shaped implant was formed and allowed to set in its insertable form. Although it was desirable to include 2 units of HGH in a suitable delivery system.

As described previously, an intraosseous composition was inserted into the osseous bore in for example a wrist fracture.

The intraosseous composition was first injected in a reduced amount along with 2 units HGH and to provide a liquidised bed to assist in the insertion of the prosthesis.

The implant was then slid down the bore in the introducer and located within the bore within the bone. The implant was then gently driven home to the bore in the bone with excess fluid material flowing up the helical ribs to the exterior to allow ready entrance of the implant into the bone.

The settable composition was then allowed to completely harden whereby the so formed composite support was provided to the osteoporotic matrix.

Example 3

A total hip replacement is presently one of the most successful operations. It can transfer a painful arthritic and crippled patient into a painless patient. One of the most significant long-term complications is however aseptic loosening. This is believed to be due to a failure of the bone cement interface in those circumstances where the bone cement polymethylmethacrylate is used. The fibrous membrane tends to develop between the bone and the adjacent metal prosthesis. Logically therefore it is desirable to prevent this membrane from forming to reduce the rate of aseptic loosening. Currently the revision rate for total hip replacement is about 10% of primary procedures. Revision surgery is particularly demanding and exposes the patient to considerable additional morbidity and mortality.

Hip prosthesis are presently available that use hydroxy apatite coatings to reduce the instance of aseptic loosening but they do not have the advantages of bone cement.

In the present invention, a composition comprising one part of HA to three to four parts of CS along with about three units HGH were mixed with about 60% of distilled water to produce a fine liquid paste. However prior to this admixture using techniques conventional to the art, an incision is made in the skin and muscle in an area proximate to the host bone. After the incision has been made, again using known techniques, the host bone is prepared to receive the prosthesis by preparing the receiving surface of the host bone to mate with the respective engaging surfaces thereof. A suitable prosthesis is selected of a size and configuration that fits tightly into the host bone. The composition in accordance with the present invention is introduced into the cavity formed in the bone whereupon the polymethylmethacrylate cement is introduced thereinto along with the prosthesis. This enhances the cement/bone interface and reduces the instance of aseptic loosening. In a preferred method layer of the inventive composition as hereinbefore set forth is preferably injected into the exposed bone surface, the excess removed and then allowed to harden. The bone cement is then introduced and the implant cemented into place.

Example 4

Spinal fusion is also possible utilising the composition in accordance with the present invention. As set forth above, appropriate surgical incision is provided to a bleeding bed of bone is exposed in the spine. A bone graft substitute formed of the composition of the invention is applied onto the surface either as a paste and/or as blocks of pre-formed material and is then supplemented by means of plates etc in accordance with conventional practices in this type of surgery. The mix is as described in Example 3 whereas suitable blocks for utilisation in spinal fusion are made in accordance with the prosthesis of Example 2.

It is apparent that from the foregoing, that the method, apparatus and composition in accordance with the present invention, provides a valuable way of treating osteoporosis among those subjects with proven bone density problems or fractures.

We claim:

1. An intraosseous injection device comprising:
    (a) an elongated shaft having a proximal and distal end and a through bore beginning at the proximal end and terminating at the distal end in a frusto-conical connector portion for releasable interconnection with cortical bone;

(b) a handle means associated with said elongated shaft at the proximal end for turning said shaft so that said shaft is releasably interconnected with the cortical bone; and (c) a syringe for the injection of an intraosseous liquid suspension into the through bore in said elongated shaft wherein said syringe is connected to said shaft.

2. The intraosseous injection device of claim 1 wherein the proximal end of said elongated shaft terminates in a hub, said hub comprising a recessed portion for the releasable engagement of manipulatable parts.

3. The intraosseous injection device of claim 2 further comprising manipulatable parts in the recessed portion of said hub.

4. The intraosseous injection device of claim 1 further comprising a means to withdraw said syringe during an injection sequence so that intraosseous liquid is applied under pressure over a selected portion of cortical bone.

5. The intraosseous injection device of claim 1 further comprising an intraosseous liquid suspension composition in said syringe wherein said intraosseous injectable composition comprises hydroxyapatite, carbonated apatite, or a mixture of hydroxyapatite and carbonated apatite, a biocompatible source of calcium ions, and a hormone selected from the group consisting of human growth hormone, insulin-like growth factor-1 and insulin-like growth factor-2 and wherein the composition is in the form of a settable injectable liquid.

6. The intraosseous injection device of claim 5 wherein said carbonated apatite or hydroxyapatite of said intraosseous injectable composition has a particle size of 30–300 μm, to obtain a spacing of about 200–250 μm between said particles in use.

7. The intraosseous injection device of claim 5 wherein said composition comprises 70 to 30% carbonated apatite or 70 to 30% hydroxyapatite, 30 to 70% calcium salt and up to 4 units of the protein, with distilled water or saline being then added to the solid admixed components in the amount of 50 to 70% by weight.

8. The intraosseous injection device of claim 5, wherein the calcium ions are derived from calcium sulphate, tricalcium phosphate, monocalcium phosphate monohydrate or calcium carbonate.

9. An intraosseous injection device comprising:

(a) an elongated shaft having a proximal and distal end and a through bore beginning at the proximal end and terminating at the distal end in a frusto-conical connector portion for releasable interconnection with cortical bone, wherein the proximal end of said elongated shaft terminates in a hub having a recessed portion for the releasable engagement of manipulatable parts comprising a needle carrying hub having a vented double hollow needle and a proximal chamber for operative interengagement with a syringe;

(b) a handle means associated with said elongated shaft at the proximal end for turning said shaft so that said shaft is releasably interconnected with cortical bone; and (c) a syringe operatively interengaged with the hub of said elongated shaft for the injection of an intraosseous liquid suspension into the through bore in said elongated shaft.

* * * * *